(12) United States Patent
Polwart et al.

(10) Patent No.: US 11,698,371 B2
(45) Date of Patent: Jul. 11, 2023

(54) METHOD FOR DETERMINING THE OUTPUT OF AN ASSAY WITH A MOBILE DEVICE

(71) Applicant: Novarum DX Limited, Cardiff (GB)

(72) Inventors: Neil Polwart, West Lothian (GB); Graham Tyrie, Edinburgh (GB); Anthony Peter Ashbrook, Edinburgh (GB)

(73) Assignee: Novarum DX Limited, Cardiff (GB)

( * ) Notice: Subject to any disclaimer, the term of this patent is extended or adjusted under 35 U.S.C. 154(b) by 706 days.

(21) Appl. No.: 15/848,076

(22) Filed: Dec. 20, 2017

(65) Prior Publication Data

US 2018/0196037 A1    Jul. 12, 2018

Related U.S. Application Data

(63) Continuation of application No. 13/980,300, filed as application No. PCT/GB2012/050717 on Mar. 30, 2012, now Pat. No. 9,903,857.

(30) Foreign Application Priority Data

Mar. 31, 2011  (GB) .................................. 1105474

(51) Int. Cl.
*G01N 21/84*     (2006.01)
*G01N 21/17*     (2006.01)
*G01N 33/50*     (2006.01)
*G01N 33/53*     (2006.01)
*G01N 33/569*    (2006.01)

(52) U.S. Cl.
CPC ..... *G01N 33/5302* (2013.01); *G01N 21/8483* (2013.01); *G01N 33/56911* (2013.01); *G01N 2021/1776* (2013.01)

(58) Field of Classification Search
CPC ....... G01N 2021/1776; G01N 21/8483; G01N 33/5302; G01N 33/56911
See application file for complete search history.

(56) References Cited

U.S. PATENT DOCUMENTS

| | | | |
|---|---|---|---|
| 2002/0146847 | A1 | 10/2002 | Lamont et al. |
| 2005/0163673 | A1 | 7/2005 | Johnson et al. |
| 2005/0178649 | A1 | 8/2005 | Liedy |
| 2005/0203353 | A1 | 9/2005 | Ma et al. |
| 2006/0222567 | A1 | 10/2006 | Hafellner |
| 2007/0287182 | A1 | 12/2007 | Morris et al. |
| 2010/0045789 | A1 | 2/2010 | Fleming et al. |
| 2010/0254581 | A1 | 10/2010 | Neeser et al. |

(Continued)

FOREIGN PATENT DOCUMENTS

| | | |
|---|---|---|
| CN | 103649731 A | 3/2014 |
| DE | 2729760 A1 | 1/1979 |

(Continued)

*Primary Examiner* — Lydia Edwards
(74) *Attorney, Agent, or Firm* — Dorton & Willis LLP; Ryan Willis

(57) ABSTRACT

A testing apparatus for performing an assay, the testing apparatus comprising: a receptacle (2) containing a reagent, the reagent being reactive to an applied test sample by developing a colour or pattern variation; a portable device (1), e.g. a mobile phone or a laptop, comprising a processor and an image capture device (3), wherein the processor is configured to process data captured by the image capture device and output a test result for the applied test sample.

10 Claims, 5 Drawing Sheets

(56) References Cited

U.S. PATENT DOCUMENTS

2011/0032525 A1  2/2011  Kurokawa et al.
2016/0047807 A1  2/2016  Koulchin et al.

FOREIGN PATENT DOCUMENTS

| EP | 2646809 B1 | 8/2018 |
|---|---|---|
| JP | 2002523030 A | 7/2002 |
| JP | 2010032447 A | 2/2010 |
| JP | 2010515877 A | 5/2010 |
| JP | 2014514547 A | 6/2014 |
| WO | 03086618 A1 | 10/2003 |
| WO | 2008049083 A2 | 4/2008 |
| WO | 2009128205 A1 | 10/2009 |
| WO | 2009144764 A2 | 12/2009 |
| WO | 2012059746 A2 | 5/2012 |

METHOD FOR DETERMINING THE OUTPUT OF AN ASSAY WITH A MOBILE DEVICE

CROSS REFERENCE TO RELATED APPLICATIONS

This application is a continuation of U.S. patent application Ser. No. 13/980,300, filed on Feb. 24, 2014 and titled "Testing Apparatus," which was a national stage application of Patent Cooperation Treaty Application Serial No. PCT/GB14/051877, filed Jun. 19, 2014, titled "Testing Apparatus," which claimed priority under 35 U.S.C. § 119 to United Kingdom Patent Application Serial No. 1105474.9, filed on Mar. 31, 2011, the disclosure of each of the foregoing applications are hereby incorporated by reference.

The present invention relates to performing testing using a mobile device, such as a mobile phone. In particular, but not exclusively, the invention relates to capturing and processing assay test data using a mobile phone.

An assay, such as a bioassay or immunoassay, is a procedure in molecular biology for testing or measuring the activity of a drug or biochemical in an organism or organic sample. Chemical, biochemical, and microbiological assays based on the development of a colour change or variation in colour hue within a defined area of a usually solid substrate are well known in a number of fields including industrial, clinical, environmental, and microbiological analysis.

Two common examples of such tests are pH indicator papers and home pregnancy tests. Typically, a colour change or the appearance of a feature on the test is assessed visually by the operator of the test using the naked eye. In the case of a pH indicator the colour change is judged by comparison to a reference scale often located on the container of the tests. In the case of a home pregnancy test, the presence or absence of a coloured line at a known location on the test strip indicates the result of the test.

These general concepts are widely applied in simple, fast, easy to use, and low cost point of use tests as well as laboratory based tests. However variations in the visual acuity of the operator can make it difficult to obtain precise results, particularly when the result is close to the limit of detection or where it must be matched to a sliding scale of hue to quantify the results. The precision, accuracy, reproducibility and repeatability of such tests can be compromised to the extent that only qualitative or semi-quantitative results are possible from such tests. Even where qualitative test results are acceptable, there is typically no formal record that the test took place for quality or evidential purposes.

It is desirable to provide testing apparatus which does not rely on the visual acuity of the operator. It is desirable to provide testing apparatus which provides quantitative rather than only qualitative test results.

It is known to use an electro-optic instrument into which the test is placed to be electronically interrogated. However, such instrumentation is often complex and custom designed for the specific application and accordingly incurs significant hardware, firmware, and software development costs. The resulting apparatus is also often relatively bulky and therefore of limited portability.

It is desirable to provide testing apparatus which is readily available, portable and/or applicable to a plurality of different tests.

Many common consumer electronic devices, such as mobile phones, can be used to capture and process images, and to output or store the image data or share the image data via a network, such as a Wi-Fi or telecommunications network. Processing of the image data is performed by the device using a number of processing techniques to produce images of good quality. There is often a trade off in the techniques employed. The processing is not configured to output only an image with the most realistic colour representation.

According to the present invention there is provided testing apparatus for performing an assay, the testing apparatus comprising:
  a receptacle containing a reagent, the reagent being reactive to an applied test sample by developing a colour or pattern variation;
  a portable device comprising a processor and an image capture device,
  wherein the processor is configured to process data captured by the image capture device and output a test result for the applied test sample.

The portable device may comprise a mobile phone, PDA, digital camera, laptop or the like. The image capture device may comprise a camera.

The testing apparatus may be configured for performing an immunoassay, such as a lateral flow immunoassay. The testing apparatus may be configured for the detection of *Legionella* bacteria.

The reagent may be solid. Alternatively, the reagent may be liquid.

The testing apparatus may be operable to transmit one or both of the data and the test result via a network.

The processor may be configured to measure the developed colour or pattern variation. Alternatively, the testing apparatus may include a remote processing device, such as a central computer, for measuring the developed colour or pattern variation and calculating the test result. The portable device may be configured to transmit the data to the remote processing device, and receive and output the calculated test result.

The remote processing device may be adapted to store one or both of the data and the test result. The remote processing device may be adapted to store one or both of the data and the test result from a plurality of assays or portable devices.

The portable device or the remote processing device may be configured to process the data and the test result from a plurality of assays or portable devices to calculate one or more group values or parameters, such as an average, a standard deviation value, a trend function or the like. The processor may be adapted to output the group value or parameter.

The portable device may be configured to modify the image to optimise the colour representation of the image.

The portable device may be configured to apply correction and/or filtering to an image to remove electronic or optical noise from the image. The portable device may be configured to discard irrelevant portions of the image to reduce processing time. The processor may be configured to reject images which are of inadequate quality.

The portable device may be configured to control one or more of the brightness, contrast, gain, colour balance and flash settings of the device during capture to achieve an optimal image for subsequent processing. The processor may be adapted to apply corrections to brightness, contrast, sharpness and colour balance after image acquisition.

The processor may be adapted to convert a colour image to a grey scale image or to a black and white image.

The portable device may be configured to compare two images and output the test result at least partially based upon the comparison.

The portable device may be configured to capture a plurality of images, each using a different exposure setting. The portable device may be configured to combine the plurality of images.

The processor may be adapted to correct the image for any rotational misalignment or skew.

The processor may be adapted to determine a degree of error associated with any rotational misalignment or skew for correcting the image.

The degree of error may be determined by comparing image features with a known geometry of the receptacle. Alternatively or in addition, the portable device may include one or more orientation sensors, such as accelerometers, and the degree of error is determined based on the signal from the orientation sensors.

The testing apparatus may be configured to prevent image capture when the degree of error is greater than a predetermined value. The testing apparatus may be configured to prevent image capture when the signal from the orientation sensors corresponds to an orientation which is outwith a predetermined range or value.

The processor may be adapted to summate one or more values of pixels in an identified region of interest.

The processor may be adapted to identify the positions of test lines. The processor may be adapted to perform peak searching within the region of interest.

The processor may be adapted to quantify the size of test or control lines using a peak height or peak area. The quantified size may be used to determine a measurement of concentration for the test. The processor may be adapted to determine a control peak. A test peak may be determined using a comparison with the control peak.

The portable device may be configured to transmit and/or store associated data along with the data. The associated data may comprise one or more of: a date or time of image capture; geolocation data for the performed assay; image capture device settings; reagent data; and user generated data.

The reagent data may comprise one or more of: a batch number; an expiration date; and calibration information. The reagent data may be provided on the receptacle. The reagent data may be presented in the form of packaging or a label. The reagent data may be provided in the form of written information which is readable by the portable device. The portable device may be adapted to interpret the written information using optical character recognition or the like. Alternatively, the reagent data may in the form of a one or two dimensional bar code.

The user generated data may comprise spreadsheet or database data, image or sound files, typed or written text or the like.

The portable device may be adapted to display instructions or guidance to the user for performing the test and/or interpreting the test result. The portable device may be adapted to provide substantially real time feedback to the user during image capture. The feedback may relate to one or more of the position, orientation, and settings used. The portable device may be configured to automatically capture the image.

The displayed instructions or guidance may comprise pre-processing steps, incubation times and the like. The portable device may include a countdown-timer for timing test durations.

The portable device may be configured to read the reagent data, such as an incubation time. The portable device may be configured to only allow the user to capture the image after testing once the incubation time has elapsed.

The portable device may be configured to display a guide or template overlay showing the outline of the reagent and/or one or more regions of interest. The feedback may be in the form of: a change of appearance, such as colour, of the guide or template overlay; or an audio or tactile indication that an image has been acquired.

The processor may be configured to utilise contrasting colours or distinct objects to process data captured by the image capture device and output the test result. The contrasting colours or distinct objects may be provided by the receptacle.

Embodiments of the present invention will now be described, by way of example only, with reference to the accompanying drawings in which.

Figure 9:
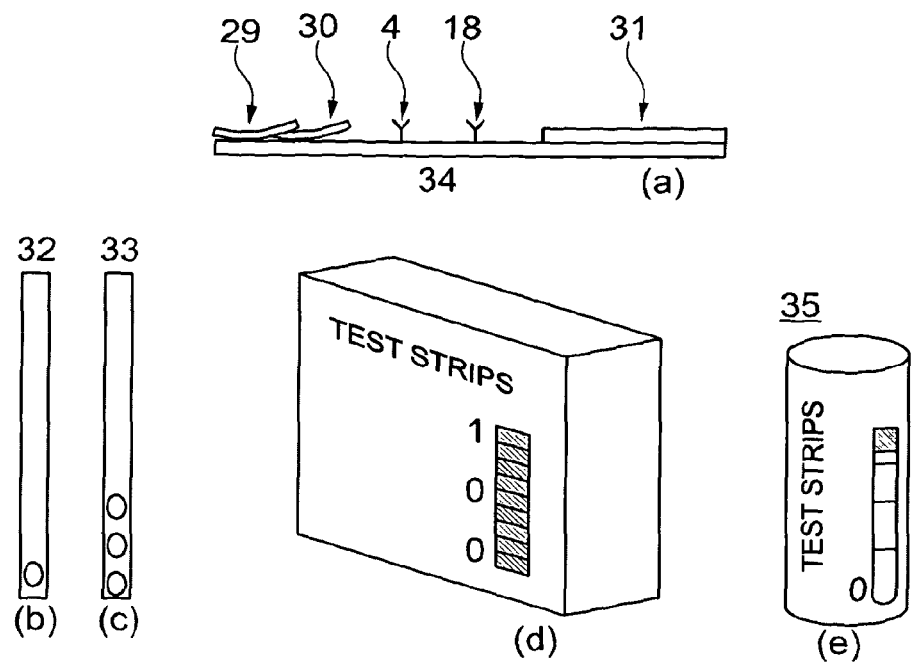
Figure 10:
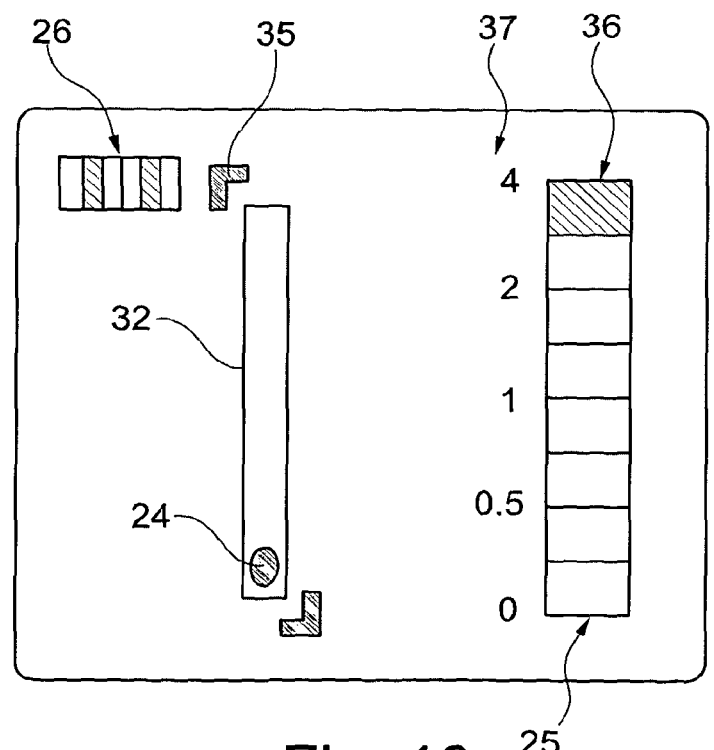

FIG. 9 shows schematic representations of example test strip and packaging configurations: (a) cross section through a typical lateral flow immunoassay (34); (b) a colorimetric test with a single region of interest; (c) a colorimetric test with multiple regions of interest; (d) and (e) examples of test packaging with comparison scales; and FIG. 10 shows an example of an image (37) being collected where both the test receptacle (32) and the reference scale information (25) are held in the same image.

Figure 1:
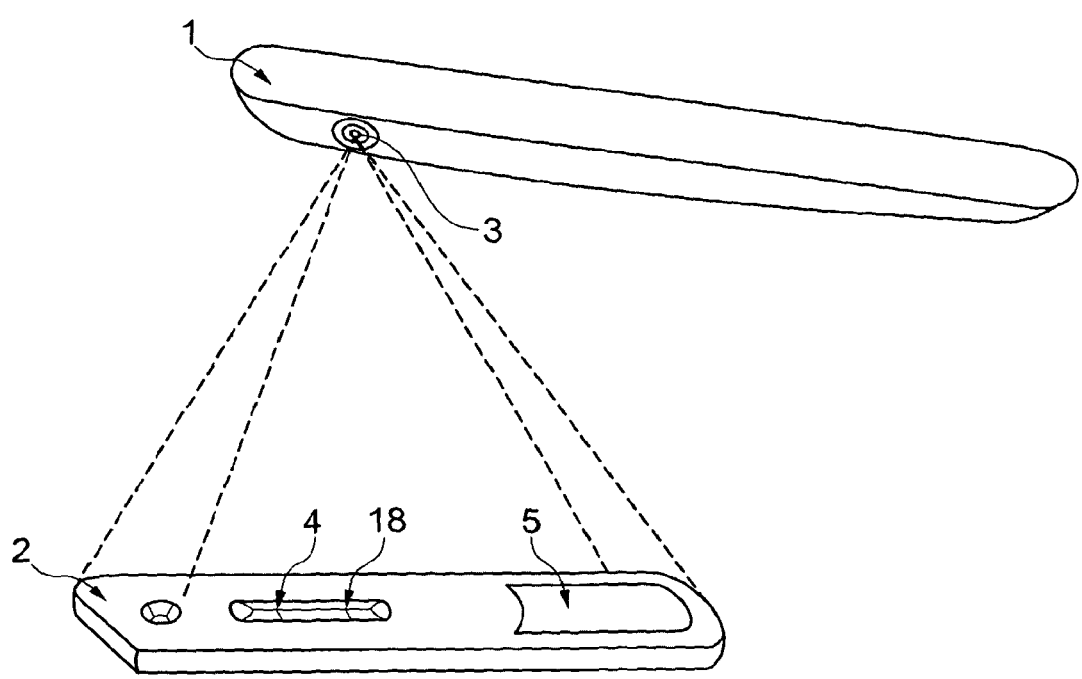
FIG. 1 is a perspective view of a testing apparatus according to the invention.
Figure 2:
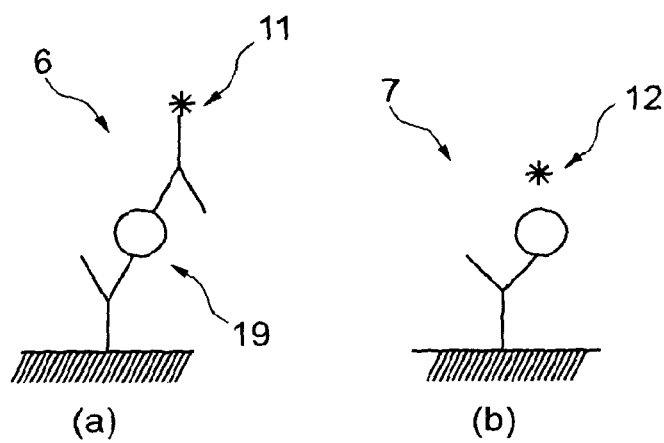
FIG. 2 is a view of (a) a sandwich assay and (b) a competitive assay.
Figure 3:
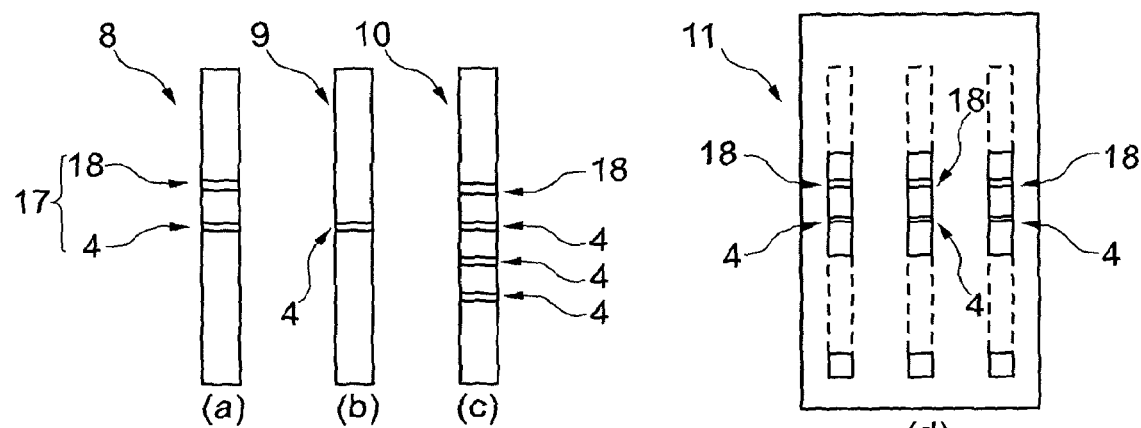
FIG. 3 is a view of an assay with (a) one control line and one test line, (b) a test line but no control line, (c) a plurality of test lines and one control line all on a single test strip, (d) a plurality of test lines and control lines on separate test strips mounted within a common housing.
Figure 4:
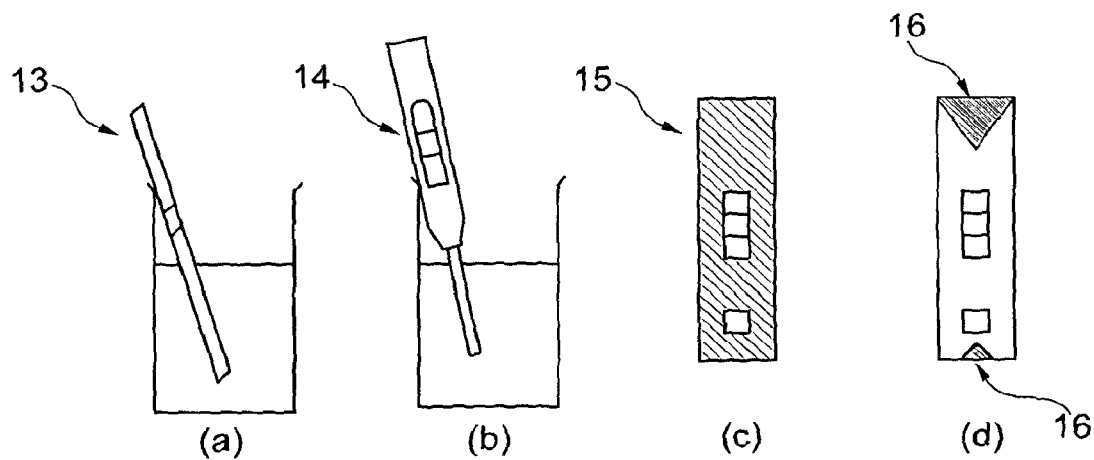
FIG. 4 is a view of an assay with (a) presented in "dipstick" format, (b) where the test strip protrudes beyond the housing in one direction, (c) contained within a housing, assays contained within a housing where some or all of the housing is coloured to enhance the contrast of the image when processed, and where markings are included on a housing to facilitate image processing.
Figure 5:
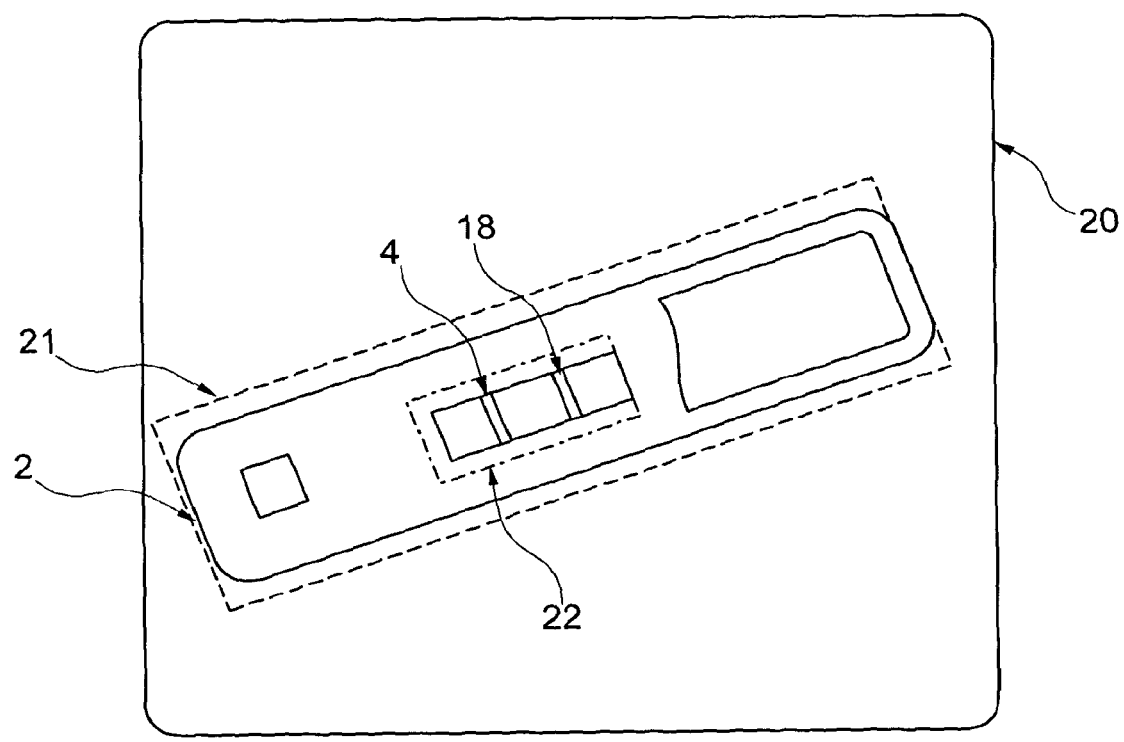
FIG. 5 is a representation of an image (20) of a test (2) captured with a portable electronic device highlighting the region of interest (21) the result window (22) and the test (4) and control line (18)
Figure 6:
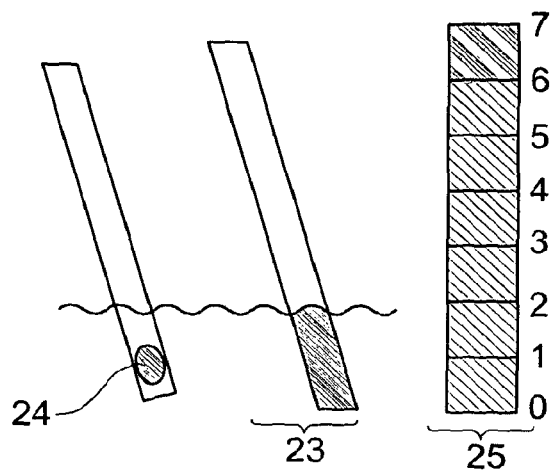
FIG. 6 shows example formats of colorimetric tests where either a distinct region (24) or the entire immersed area (23) changes colour and is compared to a reference scale (25)
Figure 7:
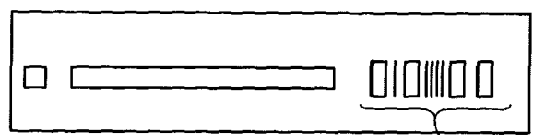
FIG. 7 is a schematic showing a possible receptacle configuration where the reference information (26) is printed on the test housing.
Figure 8:
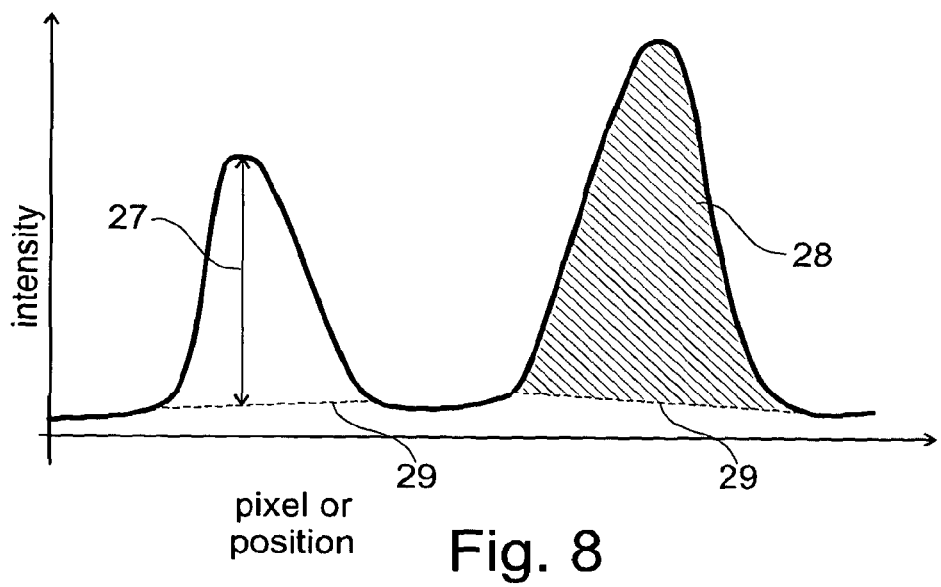
FIG. 8 shows a schematic of the signal intensity profile across a lateral flow test indicating the peak height (27) and peak area (28) measurements to the baseline (29)

FIG. 1 shows a testing apparatus for performing an assay. The testing apparatus comprises a receptacle containing a reagent in the form of a test strip, and a portable device in the form of a mobile phone [1] which has a processor and an image capture device or camera [3].

The mobile phone [1] can be used to capture and process images then share the resulting data via a telecommunications networks such as the internet. It is therefore possible to avoid the requirement for a specialist, custom designed piece of hardware and use a readily available small portable mobile consumer electronic device such as the mobile phone [1] to record and quantify the results obtained on test strip style chemical, and immunoassay devices [2].

Furthermore the device has the ability to store the time, geo-location (e.g. GPS coordinates), and any other information obtained from the extended functionality of the device [1] and associated peripherals in addition to any data captured visually (with the camera [3]), orally (as a sound file) or via typed or written notes. Such information may be stored on the device [1] for later retrieval, sent automatically or at the users request to a laboratory information management system (LIMS), or other centralised database.

In addition to measuring the test response [4], the image capture functionality of the device [1] may be used to capture and process other information about the test [2], such as batch numbers, expiration dates, or even calibration information presented on the test itself or e.g. the test packaging or labels [5]. Such information may be provided in the form of written information (interpreted via optical character recognition) or in the form of standard or modified one or two dimensional bar codes.

This invention differs from known methods in that it uses only the inbuilt hardware of the device [1] requiring no external hardware or modifications to the electronics or infrastructure of the device [1]. A key development is the inclusion of the image processing on the device [1], enabling the device [1] to be operated stand alone without internet or phone connection if desired and also for "real time" feedback to the user on the position, orientation, and image quality so that the operator can quickly capture an image of adequate quality, before any window of opportunity for a valid test result may have elapsed. Processing directly on the device enables the maximum image quality to be used. "Pre-filters" can be applied to discard irrelevant portions of the image such that processing time is minimised.

Where the dynamic range of the resulting image is inadequate for the limit of detection, or where the constraints on lighting mean exposure settings force the dynamic range to be too poor it may be desirable to capture multiple images at different exposure settings and then combine these into a single higher dynamic range 'virtual' image, using appropriate algorithms to reorient the images between frames, and to discard unwanted or low value data.

The functionality of the device [1] can also be used to display advice or guidance to the user based on the results of the test, either from a stored knowledgebase on the device [1] or by directing the user to appropriate internet resources.

Additionally the data may be processed to observe trends or patterns in the measurements.

The image processing software on the device is provided as what is commonly described as an "App". Ancillary software can be integrated with the image processing to facilitate the use, record keeping, or storage of the results. Results from colorimetric assays can be quantified and/or recording using the mobile phone [1] simply by providing the image processing software.

Similar principles may be applied to a number of different assay formats. They are described below in two broad groups, (1) assays where the sample flows over the test forming a colour change in a specific localised region of the test [2] and (2) assays where the colour change [24] is not localised, and it is then compared to a reference chart or scale [25].

Application to Lateral Flow Assays

Lateral Flow Assays, and their fabrication are well known to those skilled in the art. Assays are available commercially for a huge range of substances from small chemical species to microbiological contaminants. The principles, fabrication and operation of such devices has been described in detail previously. The technology is applicable to any assay based on the interaction of a ligand with an analyte resulting in temporary or permanent change of colour, shade or hue with a specific spatial region of a test, resulting from flow along the length of a test strip driven by capillary action. The detection method may be based on interactions involving, an antibody, an antigen, a hapten, a protein, a polynucleotide (including but not restricted to DNA and RNA), a cell, a cell fragment, a bacterium, a spore, a virus, a prion or a virion.

The use of a camera equipped mobile phone [1] to quantify the results from such assays is applicable to a broad range of lateral flow assays including but not restricted to:

both sandwich assays [6] and competitive assays [7];

assays with one control line and one test line [8], assays with a test line but no control line [9], assays with a plurality of test lines and one control line all on a single test strip [10], assays with a plurality of test lines and control lines on separate test strips mounted within a common housing [11];

assays using coloured particles as the ligand label [12];

assays using metallic nanoparticles as the coloured label [12], assays using nanoparticles in the size range 1-1000 nm, assays using nanoparticles in the size range 2-100 nm, assays using nanoparticles in the size range 10-80 nm, assays using metallic nanoparticles comprising substantially one or more elements displaying localised surface plasmon resonance such elements include: copper, silver, aluminium, gold, platinum, palladium, chromium, niobium, rhodium, and iridium;

assays using coloured polymeric particles as the ligand label [12], assays where the polymeric particles are composed mainly of latex, assays where the polymeric particles are composed mainly of polystyrene, assays where the polymeric particles are composed mainly of a polyolefin, assays where the polymeric particles are composed mainly of nylon;

assays where the colour is formed directly or indirectly by the interaction of a an enzyme with a substrate;

assays where the coloured ligand label [12] is substantially of one of the following colours: red, blue, yellow, black, or combinations thereof;

assays presented in "dipstick" format (i.e. with no plastic housing [13], or where the test strip protrudes beyond the housing in one direction [14]), assays contained within a housing [2], assays contained within a housing where the housing is formed primarily from plastic, assays contained within a housing where the housing is substantially made from cardboard or paper, assays where part or all of the housing is made from a transparent material through which the result must be viewed;

assays contained within a housing where some or all of the housing is coloured [15] to enhance the contrast of the image when subsequently processed, assays where markings [16] are included on a housing to facilitate image processing;

Following addition of a sample to a lateral flow assay, and the test being allowed to develop for a predetermined time the test will typically form one or more discrete lines [17] perpendicular to the direction of capillary flow along the test. Other patterns such as spots are also used on some tests. Most lateral flow assays in commercial use consist of at least one test line [4] and one control line [18]. However the invention is sufficiently adaptable that it can be modified to other shapes or format of assay.

The optical density (or colour intensity) of the test line [4] is related to the level of analyte [19] in the sample. In a sandwich assay the optical density may be linearly proportional to the concentration of analyte over a certain range. In a competitive assay the optical density may be inversely proportional to the analyte concentration.

The optical density, or some other measurement of colour intensity may be made using an image captured on readily available cameras [3], such as those found integrated into mobile phones, tablet PCs, netbooks, laptop computers and other consumer electronic devices [1]. The image [20] may be processed by software included within the device [1]. The exact steps and sequence of steps necessary to analyse an image [20] from a particular test may vary, but in general are likely to include some, or all of the following:

(1) identify the location and orientation [21] of the test strip/housing [2] in the image [20].
(2) identify the location of the result region [22] within the test strip/housing.
(3) identify the presence/absence of the control line [18].
(4) identify the expected location of the test line [4].
(5) identify the magnitude of the test line [4] if any.
(6) compare the magnitude of the test line [4] to the magnitude of the control line [18], or some other reference point, to calculate the test result on a real or arbitrary scale.

The software may then store, display or distribute this data using other functions and connectivity built into the consumer device. The software may append time stamps, user identities, geographic locations or other user defined information to the data for future analysis and quality control.

The software may upload data to a central database such as a Laboratory Information Management System or other data repository. The software, or database may be used to trigger certain actions, such as responding to a problem identified by an individual measurement or trend, alerting a user or other interested parties to a result or trend or providing content (via the web, email, or other communication systems including off-line communication) relevant to the test results obtained. The targeted information could include marketing, advertising or promotional material, either now or at some future date based on the outcome of results.

The software may integrate with other services on the device or via the internet such as calendars to provide reminders of regular test patterns as required.

The software may apply correction or filters to an image to remove electronic or optical noise from the image. Many standard noise filters are known to those skilled in the art. Simple noise filters may simply involve convoluting two arrays.

The software may control the brightness, contrast, gain, colour balance and flash settings of the device during capture in order to achieve an optimal image for subsequent processing. The software may capture a "non optimal" image and apply corrections to brightness, contrast, sharpness and colour balance after image acquisition.

The software may discard areas of the image which do not contain useful data to facilitate faster processing on the device.

The software may convert a colour image, to a grey scale image, or to some other form of representation to facilitate faster processing on the device.

The software may convert some or all of the image to a black and white image (binary array) to accelerate processing, for example in determining the location and edges of the region of interest [22]. Having identified the relevant portions of the image and calculated any necessary rotational correction the software may then revert to some or all of the original image file, for more detailed processing.

The software may automatically reject images which are of inadequate quality to yield useful results.

The software may guide the user during image capture to assist the user in capturing a suitable image, e.g. correctly orienting the device, correctly focussing the device, and obtaining adequate illumination. One possible solution to simplify the processing, being to display a guide or template overlay showing the outline of the test strip and/or region of interest (or simply a rectangle of the correct proportions). If the image can be processed for suitability in near real time then the correct orientation may be indicated on the screen and image capture initiated automatically. One option for this interactive feedback being the change of colour of the template, overlay or guide marks, for example by changing from red (no suitable image) to green (suitable image), thus avoiding additional 'clutter' in the display. Similarly, the software may provide the user with an audio or tactile indication that an image has been acquired, e.g. by playing a simulated "camera shutter sound", a simple beep or activating an inbuilt vibration alert within the device.

The software may also provide the user with information about the use and operation of the test, e.g. pre-processing steps, incubation times, etc. The software may even force the user to allow the full incubation time by taking images before and after testing.

The software may include a countdown-timer, for timing test durations.

Contrasting colours, e.g. on the test strip housing, and distinct shapes of housing may simplify the image processing. Where there is no housing or the housing is a similar colour to the test strip it may be preferable to place the test strip against a contrasting background during image capture.

The software may capture information about for example the form or test strip being used, its expiry date or batch-to-batch variation in sensitivity from text based data printed on the strip or packaging, from a one or two-dimensional bar code (26) on the device or from some form of printed reference colour on the strip. Such data may be stored with the eventual test results. Similar processes may be used to identify physical locations (e.g. with bar code tagged assets) or patients or test users to accelerate and reduce data entry errors. Bar code capture either taking place simultaneously with the test strip image capture or immediately before or after.

The test strip or housing may be located on the image by scanning from top to bottom and left to right for an object of approximately the right proportions. The proportions of the test strip or housing will normally be well defined and highly repeatable, and thus preloaded on the device. Features or patterns on the housing or test strip can then be used to verify the recognition.

The scale of the image can then be estimated by comparing the known dimensions of the test strip or housing to the observed features of the test.

The orientation of the device can be determined from any asymmetry in the test strip, housing shape, printing or patterns on the housing or test strip; or may be mandated to the user when capturing the image.

Standard image processing algorithms can be applied to correct for any rotational misalignment or skew. Rotational misalignment may be most simply corrected by examining a region of the image which should have a sharp contrasting straight edge (e.g. the edge of a housing) and determining the misorientation from horizontal. The whole image may then be rotated using one of a number of established algorithms which will be known to those skilled in the art. For example, rotational by sheer or rotation by area mapping. Rotation by sheer is approximately sixty times faster than rotation by area mapping but may cause distortion in the image.

Correction of images for tilt, perspective, skew etc requires that the degree of error is either known or estimated. This may be achieved by measuring distinct boundaries with reference to the expected geometry of the test housing. Alternatively or in addition, inbuilt sensors within the device may provide this information. For instance, assuming the test substrate is horizontal (e.g. on a desk or bench) the accelerometers within a phone can indicate the degree of misorientation of the device from the same plane thus facilitating software correction. Likewise those accelerometers could be used to prevent image capture if the device is not oriented within an acceptable range of angles.

With the bounds of the test strip or housing defined by criteria such as contrast, the region of interest [22] containing the result can be identified from the geometric properties of the particular test or housing.

Image information obtained from close to the boundaries of the test strip or result window may be discarded as artefacts are most commonly observed in these areas.

By summing the values of pixels in columns within the region of interest it is possible to significantly reduce the noise on the data and obtain more robust results.

When a test strip is contained within a housing there is often a positional error, particularly along the axis of flow. The exact positions of the test and control lines may therefore not be precisely controlled with respect to the edges of the housing.

The positions of the lines can be found by "peak searching" within the region of interest. A peak will be characterised by having a series of successive pixels with increasing values. By specifying limits on the expected position of peaks, minimum "intensity thresholds" for peaks, and peak width (e.g. by defining a number of successive pixels which must increase)—it is possible to filter out "noise" or artefacts which are not the real peaks. Control lines [18] on lateral flow assays will normally form characteristic strong peaks.

Test lines on lateral flow assays may be found within an expected distance from the control line. Depending upon the manufacturing process employed the line spacing may be tightly controlled. It will be possible to predict the line position from the overall scale of the image, using the known dimensions of the test strip or housing as a dimensional reference.

The size of test and control lines may be quantified as either the peak height [27] or peak area [28] (which both may or may not be measured relative to some corrected baseline [29]). These values may be used directly to compute a measurement of concentration for the test, or may be subject to further analysis.

Batch to batch, test to test, sample to sample and illumination variations may, at least partially be eliminated by measuring the relative size of the test peak compared to the control peak rather than the absolute values. For a system using an irrelevant control the response, R, may simply be considered as:

$$R=\text{Test Peak}/\text{Control Peak}.$$

For a system which does not have an irrelevant control, and where therefore the control line intensity falls as the test line intensity increases, the response may be considered as:

$$R=\text{Test Peak}/(\text{Test Peak}+\text{Control Peak})$$

From the measured response an estimate of analyte [19] concentration, may be obtained e.g. by comparing to a known calibration curve, by referring to a look up table or computation using parameters provided by the user or determined optically from the test strip, housing or packaging.

EXAMPLE 1: QUANTIFICATION OF A LATERAL FLOW DEVICE

The standard methods for detection of *Legionella* bacteria (the causative agent of Legionnaires' Disease) in water are normally slow and laboratory based. It has previously been shown that *Legionella pneumophila* serogroup 1 antigen can be detected in water using a lateral flow immunoassay, which is simple enough to be performed in the field.

The assay is performed by adding a sample of water to the test strip. The water first contacts a woven pad [29] impregnated with chemicals to adjust the pH and other properties of the sample, the sample in then drawn onto a second pad [30] by capillary action. The second pad is impregnated with antibody-coated gold nanoparticles (coloured red) specific to *Legionella pneumophila* serogroup 1. The second pad is in contact with a nitrocellulose membrane which has antibodies bound in two narrow bands perpendicular to the direction of capillary flow. The first band of antibodies [4] are specific to *Legionella* bacteria, whilst the second are raised against an irrelevant control (i.e. a material not expected to be in the sample) bound to some of the gold particles [12]. A large absorbent pad [31] in contact with the nitrocellulose wicks the water away from the nitrocellulose maintaining capillary flow.

On addition of water containing *Legionella* antigen [19] to the sample, the antigen binds to the gold nanoparticles [12] and then becomes sandwiched [6] between the antibody on the test strip and the coloured gold particles [12] forming a pink-to-red coloured line across the test. The irrelevant control particles become bound as a second line [18] across the test which functions as a control.

The antigen level can be quantified by capturing an image [20], identifying the region of interest [22] and processing that image via a number of steps to yield the relative area of the test line to the control line. By comparison to a known reference curve the approximate concentration of antigen can be estimated.

Application to Chemical/Biochemical Colorimetric Assays

In contrast to Lateral flow assays where the colour change appears at a specific location on the test, typically in chemical/biochemical or colorimetric assays all, of the test strip [23] exposed to the sample will change colour on exposure to the desired analyte. In some cases a smaller sample pad [24] will change colour whilst the rest of the device is left unchanged. Perhaps the most commonly know example of such tests is "pH paper" where the pH of a sample results in a colour change which indicates the pH of the sample. However such colorimetric indicator tests are used across a whole range of samples for a wide range of different markets, e.g. water quality testing (parameters including but not restricted to pH, chlorine, alkalinity, iron, hardness, silica, nitrates, nitrites are all routinely measured using such approaches), medical/clinical diagnostics (parameters including but not restricted to protein, ketones, glucose and blood in urine), soil testing (for example, parameters including but not restricted to pH, N/P/K nutrients), and food hygiene and processing (parameters including but not restricted to the detection of NAD/H NADP/H, quaternary ammonium disinfectants and oil quality).

A test strip may contain one [32] or more [33] tests on a single test enabling multiple chemical tests to be performed on a single device, or different test ranges to be covered with a single device.

The test result is normally obtained by visually comparing the result to a reference chart [25], often printed or included on the packaging [34, 35].

A camera equipped consumer electronic device [1] may be used to quantify the results from such assays by capturing the test strip image and processing the colour/hue information from the image. In order to correct for ambient light variations it may be most easily achieved if the reference scale [25] is also captured in the same image. The software may then identify the correct portions of the image, along with any scale/labelling information [37] and derive the estimated concentration in the sample by colour matching the reference scale [25] and the exposed or working area of the test strip [24]. Optionally the software may include a correction for differences in printing or surface finishes which are hard to match by eye.

The image processing may be simplified if the test strips and reference scale are placed on contrasting backgrounds, and if any sharp asymmetrical features [38] are included in the packaging or labelling of the test and/or reference scale such that correct orientation is more easily identified by the software.

The colour hue, or some other measurement of colour, optical density or shade may be made using an image captured on readily available cameras [3], such as those found integrated into mobile phones, tablet PCs, netbooks, laptop computers and other consumer electronic devices [1]. The image [20] may be processed by software included within the device [1]. The exact steps and sequence of steps necessary to analyse an image from a particular test may vary, but in general are likely to include some, or all of the following:

(1) identify the location and orientation of the test strip [32] and reference scale [25] in the image.
(2) identify the location of the result region(s) [24] within the test strip.
(3) Measure the colour or hue of the region of interest [24].
(4) Measure the colour or hue of various points on the reference scale [25].
(5) Correlate the hue of the region of interest to the scale obtained on the reference scale.

The software may then store, display or distribute this data using other functions and connectivity built into the consumer device. The software may append time stamps, user identities, geographic locations or other user defined information to the data for future analysis and quality control.

The software may upload data to a central database such as a Laboratory Information Management System or other data repository. The software, or database may be used to trigger certain actions, such as responding to a problem identified by an individual measurement or trend, alerting a user or other interested parties to a result or trend or providing content (via the web, email, or other communication systems including off-line communication) relevant to the test results obtained. The targeted information could include marketing, advertising or promotional material, either now or at some future date based on the outcome of results.

The software may integrate with other services on the device or via the internet such as calendars to provide reminders of regular test patterns as required.

The software may apply correction or filters to an image to remove electronic or optical noise from the image. Many standard noise filters are known to those skilled in the art. Simple noise filters may simply involve convoluting two arrays.

The software may control the brightness, contrast, gain and flash settings of the device during capture in order to achieve an optimal image for subsequent processing.

The software may discard areas of the image which do not contain useful data to facilitate faster processing on the device.

The software may convert a colour image, to a grey scale image, or to some other form of representation to facilitate faster processing on the device.

The software may convert some or all of the image to a black and white image (binary array) to accelerate processing, such as in determining the location and edges of the region of interest. Having identified the relevant portions of the image and calculated any necessary rotational correction the software may then revert to some or all of the original image file, for more detailed processing.

The software may automatically reject images which are of inadequate quality to yield useful results.

The software may guide the user during image capture to assist the user in capturing a suitable image, e.g. correctly orienting the device, correctly focussing the device, and obtaining adequate illumination. One possible solution to simplify the processing, being to display a guide or template overlay showing the outline of the test strip and/or region of interest. If the image can be processed for suitability in near real time then the correct orientation may be indicated on the screen and image capture initiated automatically. One option for this interactive feedback being the change of colour of the template, outline or guide marks, for example by changing from red (no suitable image) to green (suitable image), thus avoiding additional 'clutter' in the display. Similarly, the software may provide the user with an audio or tactile indication that an image has been acquired, e.g. by playing a simulated "camera shutter sound", a simple beep or activating an inbuilt vibration alert within the device.

The software may also provide the user with information about the use and operation of the test, e.g. pre-processing steps, incubation times, etc. The software may even force the user to allow the full incubation time by taking images before and after testing.

The software may include a countdown-tinier, for timing test durations.

Contrasting colours, e.g. on the test strip housing, and distinct shapes of housing may simplify the image processing. Where there is no housing or the housing is a similar colour to the test strip it may be preferable to place the test strip against a contrasting background during image capture.

The software may capture information about for example the form or test strip being used, its expiry date or batch-to-batch variation in sensitivity from text based data printed on the strip or packaging, from a one or two-dimensional bar code [26] on the device. Such data may be stored with the eventual test results. Such data may be captured simultaneously with the test image or immediately before or after the test image. Similar processes may be used to identify physical locations (e.g. with bar code tagged assets) or patients or test users to accelerate and reduce data entry errors.

The test strip or housing may be located on the image by scanning from top to bottom and left to right for an object of approximately the right proportions. The proportions of the test strip (or housing) will normally be well defined and highly repeatable, and thus preloaded on the device. Features or patterns on the housing or test strip can then be used to verify the recognition. The reference scale is likely to form a highly repeatable image shape/form for use in image recognition.

The scale of the image can then be estimated by comparing the known dimensions of the test strip or reference scale to the observed features of the test.

The orientation of the device can be determined from any asymmetry in the test strip, housing shape, printing or patterns [38] on the or test strip, or the packaging [34,35] or reference scale [25] included within the image; or may be mandated to the user when capturing the image.

Standard image processing algorithms can be applied to correct for any rotational misalignment or skew. Rotational misalignment may be most simply corrected by examining a region of the image which should have a sharp contrasting straight edge (e.g. the edge of a housing) and determining the misorientation from horizontal. The whole image may then be rotated using one of a number of established algorithms which will be known to those skilled in the art. For example, rotational by sheer or rotation by area mapping. Rotation by sheer is approximately sixty times faster than rotation by area mapping but may cause distortion in the image.

With the bounds of the test strip or housing defined by criteria such as contrast, the region of interest containing the result can be identified from the geometric properties of the particular test or housing.

Image information obtained from close to the boundaries of the test strip or result window may be discarded as artefacts are most commonly observed in these areas.

Averaging across the region of interest it is possible to significantly reduce the noise on the data and obtain more robust results. Some measurement of error may be obtained by averaging across multiple "sub zones" within the region of interest [24].

In order to process the region of interest into one or more numerical values which will enable comparison or matching with the reference scale it may be useful for the software, to convert the raw pixel data into its red, green and blue components, from both the region of interest and the reference scale. With very simple colour based tests this may be sufficient. Where the test is likely to produce variety of colours or where the changes are subtle it may be preferable to first convert the value to a scale more directly related to the human perception of colour, such as the Munsell System, the CIE or Hunter LAB systems. As there is no absolute scale with which to make comparison true conversion to these systems is unlikely to be facile, but by comparing to a system based on such representation, and by doing likewise with the reference scale [25] in the same image an estimate of where the value falls in the range may be possible.

Whilst described above as testing test "strips" using diffuse reflected light the overall approach is applicable to other colorimetric assays where those assays may be measuring diffuse reflected light or transmitted light, and could include vials, test tubes or cuvettes containing liquids which are themselves coloured, or which induce a colour change in the container/vessel being imaged by the consumer electronic device [1]. Similarly whilst used in a diffuse reflectance measurement the colour of surfaces or materials may be matched to a reference chart, for other scientific or testing purposes using the same general approach.

Whilst specific embodiments of the present invention have been described above, it will be appreciated that departures from the described embodiments may still fall within the scope of the present invention. For instance, whilst the present specification describes use with a usually solid substrate it will be appreciated that this approach could easily be adapted for measuring liquid samples contained within a vial, cell or other container. Where the path length through the container is fixed, and where it is places against a suitable background (such as a white piece of paper) the colour in the cell may be observed and compared to reference samples. Likewise formats such as 96- or 384-well plates in which numerous experiments are performed in parallel may be analysed using this sort of approach. Such testing may include assays for chemicals (for example testing for free chlorine using the pink colour formed on reaction with diethyl-p-phenylene diamine) or an immunoassay (for example the green colour formed in the presence of horse radish peroxidase in enzyme linked immunosorbent assays (ELISAs)).

The invention claimed is:

1. A method of performing an assay, the method comprising:
   generating image data using an image capture device of a mobile processing device when an error fails to exceed a predetermined value, where the mobile processing device is configured to generate no less than substantially real-time interactive feedback to a user of the mobile processing device to guide repositioning of the image capture device relative to a test device prior to generating the image data;
   evaluating the image data, generated from the image capture device viewing at least a portion of the test device, to determine at least one of a color, a line, and a pattern of the test device post introduction of an analyte; and,
   using the mobile processing device to automatically output a test result responsive to evaluating the image data.

2. The method of claim 1, wherein the test result is output to a mobile network comprising at least one of a Wi-Fi network and a telecommunications network.

3. The method of claim 1, wherein evaluating the image data includes measuring a developed color.

4. The method of claim 1, wherein evaluating the image data includes comparing a developed color of the image data to a predetermined color scale, where the predetermined color scale includes different testing results based upon different colors.

5. The method of claim 1, further comprising inhibiting generating the image data by the image capture device when the error exceeds the predetermined value.

6. The method of claim 1, where the mobile processing device is configured to record data for at least one of date, time, batch number, location, and calibration when the image data is generated.

7. The method of claim 5, wherein the test result is output to a mobile network comprising at least one of a Wi-Fi network and a telecommunications network.

8. The method of claim 5, wherein evaluating the image data includes measuring a developed color.

9. The method of claim 5, wherein evaluating the image data includes comparing a developed color of the image data to a predetermined color scale, where the predetermined color scale includes different testing results based upon different colors.

10. The method of claim 5, where the mobile processing device is configured to record data for at least one of date, time, batch number, location, and calibration when the image data is generated.

* * * * *